US010925144B2

(12) United States Patent
Hochwalt

(10) Patent No.: US 10,925,144 B2
(45) Date of Patent: Feb. 16, 2021

(54) ELECTRODE ASSEMBLY, DIELECTRIC BARRIER DISCHARGE SYSTEM AND USE THEREOF

(71) Applicant: NanoGuard Technologies, LLC, St. Louis, MO (US)

(72) Inventor: Mark A. Hochwalt, Chesterfield, MO (US)

(73) Assignee: Nanoguard Technologies, LLC, St. Louis, MO (US)

( * ) Notice: Subject to any disclaimer, the term of this patent is extended or adjusted under 35 U.S.C. 154(b) by 0 days.

(21) Appl. No.: 16/442,380

(22) Filed: Jun. 14, 2019

(65) Prior Publication Data

US 2020/0396819 A1  Dec. 17, 2020

(51) Int. Cl.
*H05H 1/24* (2006.01)
*A61N 1/44* (2006.01)
*A61N 1/04* (2006.01)

(52) U.S. Cl.
CPC ......... *H05H 1/2406* (2013.01); *A61N 1/0408* (2013.01); *A61N 1/0476* (2013.01); *A61N 1/44* (2013.01); *H05H 2001/2418* (2013.01)

(58) Field of Classification Search
CPC ......... H05H 1/2406; H05H 2001/2418; H05H 2001/2437; H05H 2245/121; H05H 2001/2412; A61N 1/0408; A61N 1/0476; A61N 1/44; H01T 19/00; C01B 13/11; C01B 2201/12; C01B 2201/34; B01J 2219/0849; B01D 53/32; B01D 2257/708; B01D 2259/818; B01D 2257/90
See application file for complete search history.

(56) References Cited

U.S. PATENT DOCUMENTS 3,891,561 A * 6/1975 Lowther ................. H01T 19/00
                                                422/186.2
4,524,080 A   6/1985 Sugisawa et al.
4,643,876 A   2/1987 Jacobs et al.
(Continued)

FOREIGN PATENT DOCUMENTS

CA       2 685 738        5/2010
DE   10 2014 107805       1/2015
(Continued)

OTHER PUBLICATIONS

R1, 11, Jul. 11, 2017, U.S. Appl. No. 14/921,910, US.
(Continued)

*Primary Examiner* — Xiuyu Tai
(74) *Attorney, Agent, or Firm* — Evan Law Group LLC

(57) ABSTRACT

An electrode assembly, comprising (a) a conductive electrode, having (i) a first electrode surface, (ii) a second electrode surface, opposite the first electrode surface, (iii) an electrode edge, connecting the first and second electrode surfaces, and (iv) an electrode tab, for making an electrical connection to the electrode. The electrode assembly further comprises (b) a dielectric, enclosing the first and second electrode surfaces and the electrode edge, and (c) a first working surface, on the first electrode surface, wherein the dielectric is present between the first working surface and the first electrode surface. The dielectric is conformal with the first electrode surface, the second electrode surface and the electrode edge.

18 Claims, 9 Drawing Sheets

(56) References Cited

U.S. PATENT DOCUMENTS

| | | |
|---|---|---|
| 5,184,046 A | 2/1993 | Campbell |
| 5,482,684 A | 1/1996 | Martens et al. |
| 5,656,238 A | 8/1997 | Spencer et al. |
| 5,895,587 A | 4/1999 | Sorensen |
| 6,007,770 A | 12/1999 | Peiper et al. |
| 6,093,432 A | 7/2000 | Mittal et al. |
| 6,096,564 A | 8/2000 | Denes et al. |
| 6,171,450 B1 | 1/2001 | Behnisch et al. |
| 6,403,029 B1 | 6/2002 | Schmidt |
| 6,406,759 B1 | 6/2002 | Roth |
| 6,543,460 B1 | 4/2003 | Denes et al. |
| 6,638,475 B1 | 10/2003 | Lagunas-Solar et al. |
| 6,667,007 B1 | 12/2003 | Schmidt |
| 6,991,768 B2 | 1/2006 | Keras et al. |
| 7,101,518 B1 | 9/2006 | Ko |
| 8,097,217 B2 | 1/2012 | Song |
| 8,343,422 B2 | 1/2013 | Sato et al. |
| 8,372,460 B2 | 2/2013 | Meyers et al. |
| 8,475,712 B2 | 7/2013 | Henriksson |
| 8,475,723 B2 | 7/2013 | Keras |
| 8,545,764 B2 | 10/2013 | Gesche |
| 8,551,546 B2 | 10/2013 | Rasanayagam et al. |
| 8,557,187 B2 | 10/2013 | Ehlbeck et al. |
| 8,641,977 B2 | 2/2014 | Snowball |
| 8,771,595 B2 | 7/2014 | Paskalov |
| 8,834,803 B2 | 9/2014 | Sunderland |
| 8,865,085 B2 | 10/2014 | Nam et al. |
| 8,871,145 B2 | 10/2014 | Paskalov |
| 8,920,740 B2 | 12/2014 | Yang et al. |
| 8,961,894 B2 | 2/2015 | Keener et al. |
| 8,980,190 B2 | 3/2015 | Diver et al. |
| 9,067,788 B1 | 6/2015 | Spielman et al. |
| 9,114,373 B2 | 8/2015 | Misawa et al. |
| 9,220,162 B2 | 12/2015 | Takenoshita et al. |
| 9,295,280 B2 | 3/2016 | Jacofsky et al. |
| 9,363,880 B2 | 6/2016 | Keener et al. |
| 9,408,930 B2 | 8/2016 | Keener et al. |
| 9,539,352 B2 | 1/2017 | Keener et al. |
| 9,597,422 B2 | 3/2017 | Snowball |
| 10,194,672 B2 | 2/2019 | Keener et al. |
| 2002/0129902 A1 | 9/2002 | Babayan et al. |
| 2002/0153241 A1 | 10/2002 | Niv et al. |
| 2002/0175068 A1 | 11/2002 | Hammerstrom et al. |
| 2002/0182101 A1 | 12/2002 | Koulik et al. |
| 2003/0026877 A1 | 2/2003 | Ruan et al. |
| 2003/0030374 A1 | 2/2003 | Pai |
| 2003/0039726 A1 | 2/2003 | Yuan |
| 2003/0164285 A1 | 9/2003 | Korenev |
| 2003/0168009 A1* | 9/2003 | Denes ............... H01J 37/32082 118/718 |
| 2004/0001773 A1 | 1/2004 | Schmidt |
| 2004/0037736 A1 | 2/2004 | Perruchot et al. |
| 2004/0047762 A1 | 3/2004 | Masaoka et al. |
| 2004/0050682 A1 | 3/2004 | Paskalov et al. |
| 2004/0076543 A1 | 4/2004 | Sokolowski et al. |
| 2004/0131496 A1 | 7/2004 | Goetzelmann et al. |
| 2004/0141278 A1 | 7/2004 | Grosse et al. |
| 2004/0208804 A1 | 10/2004 | Hall et al. |
| 2004/0216845 A1 | 11/2004 | Golkowski |
| 2004/0250688 A1 | 12/2004 | Farkas et al. |
| 2005/0019209 A1 | 1/2005 | Burger et al. |
| 2005/0056596 A1 | 3/2005 | Paskalov et al. |
| 2005/0109739 A1 | 5/2005 | Destrez et al. |
| 2005/0127843 A1 | 6/2005 | Koulik et al. |
| 2005/0196315 A1 | 9/2005 | Babko-Malyi et al. |
| 2005/0274122 A1 | 12/2005 | Chang et al. |
| 2006/0027539 A1 | 2/2006 | Golkowski |
| 2006/0060464 A1 | 3/2006 | Chang |
| 2006/0137212 A1 | 6/2006 | Nomine |
| 2006/0251550 A1 | 11/2006 | Keras |
| 2007/0020159 A1 | 1/2007 | Tsui |
| 2007/0104610 A1 | 5/2007 | Houston et al. |
| 2007/0261555 A1 | 11/2007 | Aubert |
| 2007/0270833 A1 | 11/2007 | Bonutti et al. |
| 2008/0006536 A1 | 1/2008 | Cuomo et al. |
| 2008/0063559 A1 | 3/2008 | Alexander et al. |
| 2008/0099406 A1 | 5/2008 | Ruan et al. |
| 2008/0173621 A1 | 7/2008 | Kuo |
| 2008/0193330 A1 | 8/2008 | Hotta et al. |
| 2008/0258648 A1 | 10/2008 | Bleukx et al. |
| 2008/0260578 A1 | 10/2008 | Engemann et al. |
| 2008/0292497 A1 | 11/2008 | Vangeneugden et al. |
| 2008/0314243 A1 | 12/2008 | Chan et al. |
| 2009/0121637 A1 | 5/2009 | Laroussi |
| 2009/0159461 A1 | 6/2009 | McCutchen et al. |
| 2009/0274592 A1 | 11/2009 | Bergeron |
| 2009/0288559 A1 | 11/2009 | Kuo |
| 2009/0297409 A1 | 12/2009 | Buchanan et al. |
| 2009/0304562 A1 | 12/2009 | Hayashi et al. |
| 2010/0006121 A1 | 1/2010 | Baxter et al. |
| 2010/0032285 A1 | 2/2010 | Thomas et al. |
| 2010/0119670 A1 | 5/2010 | Mazzariello |
| 2010/0206232 A1 | 8/2010 | Duclos et al. |
| 2010/0209293 A1 | 8/2010 | Ikawa et al. |
| 2010/0304146 A1 | 12/2010 | Krebs et al. |
| 2011/0014330 A1 | 1/2011 | Meyers et al. |
| 2011/0115415 A1 | 5/2011 | Hong |
| 2011/0116967 A1 | 5/2011 | Roy et al. |
| 2011/0251604 A1 | 10/2011 | Staack et al. |
| 2011/0268850 A1 | 11/2011 | Rasanayagam et al. |
| 2012/0000782 A1 | 1/2012 | Hong |
| 2012/0093687 A1 | 4/2012 | Snowball |
| 2012/0156093 A1 | 6/2012 | Kitano |
| 2012/0156340 A1 | 6/2012 | Rasanayagam et al. |
| 2012/0156341 A1 | 6/2012 | Rasanayagam et al. |
| 2012/0183437 A1 | 7/2012 | Keener et al. |
| 2012/0213664 A1 | 8/2012 | Diver et al. |
| 2013/0053761 A1 | 2/2013 | Morfill et al. |
| 2013/0104742 A1 | 5/2013 | Deo et al. |
| 2013/0105025 A1 | 5/2013 | Fehr et al. |
| 2013/0164173 A1 | 6/2013 | Norris |
| 2013/0189156 A1 | 7/2013 | Keener et al. |
| 2013/0196099 A1 | 8/2013 | Sakamoto et al. |
| 2013/0319460 A1 | 12/2013 | Schneider et al. |
| 2013/0345620 A1* | 12/2013 | Zemel ............... A61B 18/042 604/24 |
| 2014/0044595 A1 | 2/2014 | Keener et al. |
| 2015/0150297 A1 | 6/2015 | Kim et al. |
| 2015/0273094 A1 | 10/2015 | Keener et al. |
| 2015/0327430 A1 | 11/2015 | Dong et al. |
| 2015/0327562 A1 | 11/2015 | Zwijack |
| 2015/0342397 A1 | 12/2015 | Deo et al. |
| 2015/0373923 A1 | 12/2015 | Ferrell et al. |
| 2016/0262410 A1 | 9/2016 | Hoefnagels |
| 2017/0000167 A1 | 1/2017 | Corrigan |
| 2017/0112157 A1 | 4/2017 | Keener et al. |
| 2017/0133205 A1 | 5/2017 | Ehlbeck et al. |

FOREIGN PATENT DOCUMENTS

| | | |
|---|---|---|
| EP | 1 884 248 | 2/2008 |
| EP | 2 374 753 | 10/2011 |
| EP | 3 383 144 | 3/2018 |
| RU | 2102084 | 1/1998 |
| RU | 2199349 | 2/2003 |
| RU | 2254143 | 6/2005 |
| WO | 1997/18343 | 5/1997 |
| WO | 1997/022369 | 6/1997 |
| WO | 1998/51608 | 11/1998 |
| WO | 1998/51609 | 11/1998 |
| WO | 2002/022447 | 4/2000 |
| WO | 2000/054819 | 9/2000 |
| WO | 2002/078749 | 10/2002 |
| WO | 2006/004399 | 1/2006 |
| WO | 2007/067924 | 6/2007 |
| WO | 2007/124910 | 11/2007 |
| WO | 2007/124945 | 11/2007 |
| WO | 2008/072170 | 6/2008 |
| WO | 2008/096292 | 8/2008 |
| WO | 2008/126068 | 10/2008 |
| WO | 2008/127135 | 10/2008 |
| WO | 2008/144499 | 11/2008 |
| WO | 2009/040130 | 4/2009 |
| WO | 2009/041861 | 4/2009 |

(56) References Cited

FOREIGN PATENT DOCUMENTS

| | | |
|---|---|---|
| WO | 2009/098662 | 8/2009 |
| WO | 2011/116984 | 9/2011 |
| WO | 2011/123512 | 10/2011 |
| WO | 2012/038669 | 3/2012 |
| WO | 2012/079858 | 6/2012 |
| WO | 2012/097987 | 7/2012 |
| WO | 2012/112042 | 8/2012 |
| WO | 2012/113568 | 8/2012 |
| WO | 2012/125435 | 9/2012 |
| WO | 2012/130197 | 10/2012 |
| WO | 2013/076102 | 5/2013 |
| WO | 2013/076458 | 5/2013 |
| WO | 2014/135254 | 9/2014 |
| WO | 2014/152169 | 9/2014 |
| WO | 2015/091221 | 6/2015 |
| WO | 2016/007000 | 1/2016 |
| WO | 2016/140447 | 9/2016 |
| WO | 2017/019621 | 2/2017 |
| WO | 2017/070240 | 4/2017 |
| WO | 2018/045378 | 3/2018 |

OTHER PUBLICATIONS

R2, 3, Aug. 30, 2017, U.S. Appl. No. 14/921,910, US.
R3, 22, Oct. 18, 2017, U.S. Appl. No. 14/921,920, US.
R4, 4, Jan. 4, 2018, 16788620.9, EP.
R5, 40, Sep. 25, 2018, 16788620.9, EP.
R6, 15, Sep. 28, 2018, U.S. Appl. No. 14/921,910, US.
R7, 23, Feb. 1, 2019, 201610939647.X, CN.
R8, 2, Feb. 21, 2019, 16788620.9, EP.
R9, 5, Apr. 12, 2019, MX/a/2018/004893, MX.
R10, 1, Jun. 17, 2019, 3,039,902, CA.
R11, 8, Jul. 5, 2019, 201827013136, IN.
R12, 13, Jul. 25, 2019, 2018-520174, JP.
R13, 9, Aug. 26, 2019, 201610939647.X, CN.
R14, 21, Sep. 17, 2019, U.S. Appl. No. 16/215,187, US.
R15, 4, Sep. 19, 2019, 10-2018-7012556, KR.
R16, 3, Sep. 19, 2019, 19155626.5, EP.
R17, 40, Apr. 9, 2018, 16788620.9, EP.
R18, 40, Sep. 25, 2018, 16788620.9, EP.
R19, 4, Dec. 10, 2019, 10-2018-7012556, KR.
R20, 12, Dec. 6, 2019, 2018118775, RU.
R21, 4, Jan. 7, 2020, 2018-520174, JP.
R22, 11, Jan. 22, 2020, U.S. Appl. No. 16/215,187, US.
R23, 5, Jan. 21, 2020, 201610939647.X, CN.
R24, 10, Feb. 13, 2020, 19189770.1, EP.
R25, 8, Feb. 25, 2020, 19155626.5, EP.
R27, 16, Apr. 1, 2020, 2018118775, RU.
R28, 1, May 17, 2019, 2018/03358, ZA.
R29, 1, Sep. 11, 2019 MX/a/2018/004893, MX.
R30, 2, Feb. 17, 2020, 10-2018-7012556, KR.
International Search Report dated Jan. 25, 2017 for PCT application No. PCT/US2016/057753, 12 pages.
Connolly, J. et al., "Characterization and antimicrobial efficacy against E. coli of a helium/air plasma at atmospheric pressure created in a plastic package", Journal of Physics D: Applied Physics, vol. 46, No. 3, pp. 1-12, (2013).
Misra, N.N. et al., "In-package atmospheric pressure cold plasma treatment of cherry tomatoes", Journal of Bioscience and Bioengineering, vol. 118, No. 2, pp. 177-182, (2014).
Chiper, A.S. et al., "Atmospheric pressure plasma produced inside a closed package by a dielectric barrier discharge in Ar/CO$_2$ for bacterial inactivation of biological samples", Plasma Sources Science and Technology, vol. 20, No. 2, pp. 1-10, (2011).
Kolb, J.F. et al., "Cold atmospheric pressure air plasma jet for medical applications", Applied Physics Letters, vol. 92, pp. 241501-1-241501-3, (2008).
Winter, J. et al., "Aspects of UV-absorption spectroscopy on ozone in effluents of plasma jets operated in air", Journal of Physics D: Applied Physics, vol. 45, pp. 1-7, (2012).

Katsonis, K. et al., "Global modeling of N$_2$O discharges: Rate coefficients and comparison with ICP and glow discharges results", International Journal of Aerospace Engineering, vol. 2013, pp. 1-25, (2013).
"Aflatoxin", Wikipedia, pp. 1-5, found at https://en.wikipedia.org/wiki/Aflatoxin, printed on Jul. 10, 2015.
Lunov, O. et al., "Cell death induced by ozone and various non-thermal plasmas: therapeutic perspectives and limitations", Scientific Reports, vol. 4, pp. 1-11, (2014).
"Volt", Wikipedia, pp. 1-4, found at https://en.wikipedia.org/wiki/Volt, Printed on Jul. 10, 2015.
Moiseev, T. et al., "Post-discharge gas composition of a large-gap DBD in humid air by UV-Vis absorption spectroscopy", Plasma Sources Science and Technology, vol. 23, pp. 1-13, (2014).
"Endospore", Wikipedia, pp. 1-6, found at https://en.wikipedia.org/wiki/Endospore, Printed on Sep. 10, 2017.
Trombete, Fm. et al., "Efficacy of ozone treatment on mycotoxins and fungal reduction in artificially contaminated soft wheat grains", Journal of Food Processing and Preservation, vol. 41, No. 3, (2017). Abstract Only.
McKenzie, K.S. et al., "Oxidative degradation and detoxification of mycotoxins using a novel source of ozone", Food and Chemical Toxicology, vol. 35, No. 8, pp. 807-820, (1997). Abstract Only.
Wang L. et al., "Effect of ozone treatment on deoxynivalenol and wheat quality", PLoS One, vol. 11, No. 1, pp. 1-13, (2016).
McDonougha, M.X. et al., "Ozone application in a modified screw conveyor to treat grain for insect pests, fungal contaminants, and mycotoxins", Journal of Stored Products Research, vol. 47, No. 3, pp. 249-254, (2011).
Tiwari, B.K. et al., "Application of ozone in grain processing", Journal of Cereal Science, vol. 51, issue 3, pp. 248-255, (2010). Abstract Only.
Guzel-Seydima, Z.B. et al., "Use of ozone in the food industry", LWT-Food Science and Technology, vol. 37, No. 4, pp. 453-460, (2004).
"Listeria monocytogenes", Wikipedia, pp. 1-7, found at https://en.wikipedia.org/wiki/Listeria_monocytogenes, printed on Jul. 10, 2015.
"Bacillus atrophaeus", Wikipedia, pp. 1-2, found at https://en.wikipedia.org/wiki/Bacillus_atrophaeus, printed on Jul. 10, 2015.
"Salmonella enterica", Wikipedia, pp. 1-3, found at https://en.wikipedia.org/wiki/Salmonella_enterica, printed on Jul. 10, 2015.
"Clostridium botulinum", Wikipedia, pp. 1-6, found at https://en.wikipedia.org/wiki/Clostridium_botulinum, printed on Jul. 10, 2015.
"Sterilization (microbiology)", Wikipedia, pp. 1-10, found at https://en.wikipedia.org/wiki/Sterilization_(microbiology), printed on Jul. 10, 2015.
Food and Drug Administration, "Guidance for industry for the submission documentation for sterilization process validation in applications for human and veterinary drug products", Office of Training and Communication Division of Drug Information, CDER, FDA, pp. 1-18, (1994).
Chaven, S. et al., "Food safety systems for low-acid aseptic beverages", Food Safety Magazine, pp. 1-6, found at www.foodsafetymagazine.com/magazine-archive1/junejuly-2012/food-safety-systems-for-low-acid-aseptic-beverages/, (2012).
US Food and Drug Administration, "Guidance for Industry: Juice HACCP hazards and controls guidance first edition: Final guidance", pp. 1-67, (2004).
Lopez, J.L., "Dielectric barrier discharge, ozone generation, and their applications", Complex Plasmas Summer Institute, pp. 1-93, (2008).
Pankaj, S.K. et al., "Degradation kinetics of organic dyes in water by high voltage atmospheric air and modified air cold plasma", Water Science & Technology, pp. 1-8, (2017).
Pankaj, S.K. et al., "Effect of high voltage atmospheric cold plasma on white grape juice quality", Journal of the Science of Food and Agriculture, vol. 97, pp. 4016-4021, (2017).
Yepez, X.V. et al., "High-voltage atmospheric cold plasma (HVACP) hydrogenation of soybean oil without trans-fatty acids", Innovative Food Science and Emerging Technologies, vol. 38, pp. 169-174, (2016).

(56) References Cited

OTHER PUBLICATIONS

Wan, Z. et al., "High voltage atmospheric cold plasma treatment of refrigerated chicken eggs for control of Salmonella enteritidis contamination on egg shell", LWT—Food Science and Technology, vol. 76, pp. 124-130, (2017).
Xu, L. et al., "Microbial inactivation and quality changes in orange juice treated by high voltage atmospheric cold plasma", Food Bioprocess Technology, vol. 10, pp. 1778-1791, (2017).
McClurkin-Moore, J.D. et al., "The effect of high-voltage atmospheric cold plasma treatment on the shelf-life of distillers wet grains", Food Bioprocess Technology, vol. 10, pp. 1431-1440, (2017).
Pankaj, S.K. et al., "Cold plasma: background, applications and current trends", Current Opinion in Food Science, vol. 16, pp. 49-52, (2017).
Shi, H. et al., "Reduction of aflatoxin in corn by high viltage atmospheric cold plasma", Food Bioprocess Technology, vol. 10, pp. 1042-1052, (2017).
Misra, N.N. et al., "The effects of nonthermal plasma on chemical quality of strawberries", Postharvest Biology and Technology, vol. 110, pp. 197-202, (2015).
Hojnik, N. et al., "Mycotoxin decontamination of food: Cold atmospheric pressure plasma versus "classic"decontamination", Toxins, vol. 9, No. 151, pp. 1-19, (2017).
Siciliano, I. et al., "Use of cold atmospheric plasma to detoxify hazelnuts from aflatoxins", Toxins, vol. 8, No. 125, pp. 1-10, (2016).
Ma, H. et al., "Non-thermal pasteurization of liquid foods using non-thermal plasma", Transactions of the CSAE, vol. 18, No. 5, pp. 155-159, (2002).
Li, Y. et al., "Degradation of aflatoxin $B^1$ in agricultural products by low temperature radio frequency plasma", Science and Technology of Cereals, Oils and Foods, vol. 22.5, pp. 1-11, (2014).
Chen, Y., "High voltage atmospheric cold plasma treatment of refrigerated chicken eggs for control of Salmonella enteritidis on external surfaces", Purdue University, Theses and Dissertations, pp. 1-209, (2014).
Morfill, G.E. et al., "Nosocomial infections—a new approach towards preventive medicine using plasmas", New Journal of Physics, vol. 11, 115019, pp. 1-10, (2009).
Lu, H. et al., "Bacterial inactivation by high-voltage atmospheric cold plasma: influence of process parameters and effects on cell leakage and DNA", Journal of Applied Microbiology, vol. 116, pp. 784-794, (2013).
Lopez, M. et al., "A review on non-thermal atmospheric plasma for food preservation: Mode of action, determinants of effectiveness, and applications", Frontiers in Microbiology, vol. 10, pp. 1-21, (2019).
Extended European Search Report dated Feb. 25, 2020 for European application No. 19155626.5, 8 pages.
"Ozone effects on pathogens", Ozone Solutions, 5 pages, downloaded on Mar. 13, 2020, found at www.ozonesolutions.com/blog/ozone-effects-on-pathogens-bc5a25/.
"Ozone as a disinfectant to destroy pathogens, like the coronavirus", Ozone Solutions, 2 pages, downloaded on Mar. 13, 2020, found at www.ozonesolutions.com/blog/ozone-as-a-disinfectant-to-destroy-pathogens-like-the-coronavirus/.
Foarde, K. et al., "Ozone antimicrobial efficacy", U.S. Environmental Protection Agency, National Risk Management Research Laboratory, pp. 1-13, (2007).
Pradeep, P. et al., "Non-thermal plasmas (NTPs) for inactivation of viruses in abiotic environment", Research Journal of Biotechnology, vol. 11, No. 6, pp. 91-96, (2016).
Wu, Y. et al., "MS2 virus inactivation by atmospheric-pressure cold plasma using different gas carriers and power levels", Applied and Environmental Microbiology, vol. 81, No. 3, pp. 996-1002, (2015).
Yasuda, H. et al., "Biological evaluation of DNA damage in bacteriophages inactivated by atmospheric pressure cold plasma", Plasma Processes and Polymers, vol. 7, pp. 301-308, (2010).

Alshraiedeh, N.H. et al., "Atmospheric pressure, nonthermal plasma inactivation of MS2 bacteriophage: effect of oxygen concentration on virucidal activity", Journal of Applied Microbiology, vol. 115, pp. 1420-1426, (2013).
Bae, S.C. et al., "Inactivation of murine norovirus-1 and hepatitis A virus on fresh meats by atmospheric pressure jets", Food Research International, vol. 76, pp. 342-347, (2015).
Cowling, B.J. et al., "Aerosol transmission is an important mode of influenza A virus spread", Nature Communications, vol. 4, 1935, pp. 1-6, (2013).
Kuzmanovic, D.A. et al., "Bacteriophage MS2: Molecular weight and spatial distribution of the protein and RNA components by small-angle neutron scattering and virus counting", Structure, vol. 11, pp. 1339-1348, (2003).
Wolf, C. et al., "Proxies to monitor the inactivation of viruses by ozone in surface water and wastewater effluent", Water Research, vol. 166, (2019).
Brie, A. et al., "Inactivation of murine norovirus and hepatitis A virus on fresh raspberries by gaseous ozone treatment", Food Microbiology, vol. 70, pp. 1-6, (2018).
Hudson, J.B. et al., "Development of a practical method for using ozone gas as a virus decontaminating agent", Ozone: Science & Engineering, vol. 31, No. 3, pp. 216-223, (2009).
Muller, J.A. et al., "Development of a high-throughput colorimetric Zika virus Infection Assay", Medical Microbiology and Immunology, vol. 206, issue 2, pp. 175-185, (2017).
World Health Organization, "Zika virus Situation Report—Feb. 5, 2016", 6 pages, (2016).
Rasmussen, S.A. et al., "Zika virus and birth defects—reviewing the evidence for causality", The New England Journal of Medicine, pp. 1-7, (2016).
Muller, J.A. et al., "Inactivation and environmental stability of Zika virus", Emerging Infectious Diseases, vol. 22, No. 9, pp. 1685-1687, (2016).
Aubry, M. et al., "Inactivation of Zika virus in plasma with amotosalen and ultraviolet A illumination", Transfusion, vol. 56, pp. 33-40, (2016).
Butot, S. et al., "Procedure for rapid concentration and detection of enteric viruses from berries and vegetables", Applied and Environmental Microbiology, vol. 73, No. 1, pp. 186-192, (2007).
Woolston, J. et al., "Bacteriophage lytic for salmonella rapidly reduce salmonella contamination on glass and stainless-steel surfaces", Bacteriophage, vol. 3, issue 3, pp. e25697-1-.e25697-6, (2013).
Carey-Smith, G.V. et al., "Isolation and characterization of bacteriophages infecting salmonella spp.", FEMS Microbiology Letters, vol. 258, pp. 182-186, (2006).
Soffer, N. et al., "Bacteriophages safely reduce salmonella contamination in pet food and raw pet food ingredients", Bacteriophage, vol. 6, No. 3, pp. e1220347-1-e1220347-8, (2016).
Shin, H. et al., "Receptor diversity and host interaction of bacteriophages infecting *Salmonella enterica* serovar typhimurium", Plos One, vol. 7, issue 8, pp. e43392-1-e43392-11, (2012).
"Influenza type A viruses—Avian influenza (Flu)", Centers for Disease Control and Prevention, 2 pages, found at www.cdc.gov/flu/avianflu/influenza-a-virus-subtypes.htm, (2020).
Dow Corning, Product Information, "Dow Corning® 3-4207 Dielectric Tough Gel", 3 pages, (2017).
Cock, I. et al., "A modified MS2 bacteriophage plaque reduction assay for the rapid screening of antiviral plant extracts", Pharmacognosy Research, vol. 2, issue 4, pp. 221-228, (2010).
Acl Inc., Product Information, "8690 Staticide Acrylic Conformal Coating", 1 page, (2016).
Corning Gorilla Glass, Product Information, "Corning Gorilla Glass 3", 2 pages, (2016).
ResinLab, an Ellsworth Adhesives Company, Product Information, "Technical Data Sheet EP750 Clear", 3 pages, (2016).
ResinLab, an Ellsworth Adhesives Company, "Safety Data Sheet for EP750 Clear A", pp. 1-13, (2015).
ResinLab, an Ellsworth Adhesives Company, "Safety Data Sheet for EP750 Clear B", pp. 1-9, (2015).
Acculam Laminated Thermoset Plastic, Product Data Sheet, "Acculam® Epoxyglas G10, FR4", 1 page, (2017).

(56) References Cited

OTHER PUBLICATIONS

Encon2.3 Fact Sheet, "Improving energy efficiency in grain drying", 5 pages, (2012).
Biomin, "World Mycotoxin Survey, The global threat", 5 pages, (2019).
SciFinder Search Report on "Inactivation of Viruses using Ozone", pp. 1-14, generated on Feb. 10, 2020.
U.S. Appl. No. 16/215,187, mailed Nov. 16, 2020, 13 pages.
U.S. Appl. No. 17/017,517, filed Sep. 10, 2020.
International Search Report dated Oct. 27, 2020 for PCT application No. PCT/US2020/036833, 12 pages.

* cited by examiner

ELECTRODE ASSEMBLY, DIELECTRIC BARRIER DISCHARGE SYSTEM AND USE THEREOF

BACKGROUND

Plasmas have been used for decontamination and sterilization. Plasma, a fourth state of matter distinguished from gas, liquid and solid, may be produced through electrical discharge, for example electrical discharge through a gas. Although all plasmas contain electrons, ions and neutral species, they will have different properties depending on the composition of the gas used to prepare the plasma, as well as the electrical and structural configuration of the device used to produce the plasma.

One type of plasma is high-voltage cold plasma (HVCP), which may be prepared using dielectric barrier discharge (DBD) systems. HVCP may be prepared using non-equilibrium breakdown of a gas, using voltages preferably of 30 kV to 500 kV, typically at a frequency of 50 or 60 Hz with a DBD system. HVCP has not been studied as well as other types of plasmas, such as thermal plasma or RF plasmas. Consequently, there is presently no theory which explains the properties of these plasmas, nor the various excited and reactive species produced in such plasma. Over the last decade experimental examination of HVCP has been carried out to study this plasma.

Direct exposure of materials to HVCP has been studied. Of particular relevance are the studies exposing biological products and contaminants to HVCP, where the biological products are sealed inside packages and the HVCP is produced inside the package. In such studies, packaged foods such as produce and other materials were sterilized in a short period of time. The product inside the packages comes into direct contact with the plasma. Since the packages are sealed, reactive gas produced in the plasma remains in contact with the product indefinitely, is not diluted or dispersed, and the packaged product is protected from recontamination, dramatically extending the shelf life of the products, such as fruits and vegetables. See, for example, U.S. Pat. Pub., Pub. Nos. 2013/0189156 and 2014/0044595, both to Keener et al.

U.S. Pat. No. 10,194,672 to Keener et al. describes the use of reactive gas produced by HVCP. The reactive gas is able to sterilize or pasteurize surfaces even when transported a significant distance from the DBD system where the plasma is produced. Furthermore, the reactive gas is able to break down some organic and biological materials, such as mycotoxins. Unlike HVCP produced within a package, there is no direct exposure of the product to the HVCP, the contact time of the reactive gas with the product is limited. Furthermore, because the reactive gas is transported away from the DBD system where the HVCP is produced, it is diluted by both diffusion into the surrounding gas, and mixed with the surrounding gas and/or the working gas. Since the reactive gas is transported away from the DBD system, much larger volumes of product may be exposed to the reactive gas, in batch processes or continuous processes. In addition, large scale disinfection, such as disinfection of a surgical suite, may also be carried out.

SUMMARY

In a first aspect, the present invention is an electrode assembly, comprising (a) a conductive electrode, having (i) a first electrode surface, (ii) a second electrode surface, opposite the first electrode surface, (iii) an electrode edge, connecting the first and second electrode surfaces, and (iv) an electrode tab, for making an electrical connection to the electrode. The electrode assembly further comprises (b) a dielectric, enclosing the first and second electrode surfaces and the electrode edge, and (c) a first working surface, on the first electrode surface, wherein the dielectric is present between the first working surface and the first electrode surface. The dielectric is conformal with the first electrode surface, the second electrode surface and the electrode edge.

Definitions

All current described herein is alternating current, specified as volts (V) and kilovolts (kV) root mean squared (RMS).

A cold plasma refers to plasma which has a temperature of at most 40° C. above the temperature of the gas used to prepare the plasma (that is, the working gas), more preferably a temperature of at most 20° C. above the temperature of the gas used to prepare the plasma.

High-voltage cold plasma (HVCP) means a cold plasma prepared using a dielectric barrier discharge (DBD) system, using voltages of at most 500 kV, with a frequency at most to 1000 Hz, prepared from a gas having a pressure of 10 to 50000 Torr, such as 760 Torr (atmospheric pressure). HVCP is not a thermal plasma, is not a microwave plasma and is not a radio frequency (RF) plasma. HVCP plasmas are prepared under non-equilibrium breakdown conditions.

Reactive gas means the gas produced by an HVCP, including excited and chemically reactive species, but not those species which dissipate in 0.2 seconds or less. The composition of a reactive gas will change over time as excited species dissipate and chemical reactions within the reactive gas take place. Reactive gas is the gas that may be moved away from the DBD system that is producing an HVCP. A reactive species or excited species is considered to be present in a reactive gas if it can be detected using spectroscopy.

Dielectric barrier discharge (DBD), or a DBD system, means a system having at least two electrodes separated by a dielectric barrier, and may have more electrodes, where a dielectric barrier is present between each electrode, to prevent charge generated in the gas by a discharge from reaching an electrode.

An "electrode" is a conductive material connected to a power source or ground.

"Conformal" means that the conformal material is entirely in contact with the surface of the material or object on which it is present, following its surface including curves, depressions and bumps.

The term "hot" is used to identify an electrode connected to high voltage, while "ground" is used to identify an electrode connected to ground. These terms are also used to identify electrodes which will be connected to high voltage and ground, respectively, when in use to produce an HVCP.

"Radius of curvature parallel to the electrode surface" mean that all the radii of the curvature are parallel to the electrode surface. This is the curvature that is observer at the corners of an electrode surface when looking down onto the surface (such as in FIG. 1).

"Radius of curvature perpendicular to the electrode surface" means that not all the radii of the curvature are parallel to an electrode surface. This is the curvature that is observer when viewing the electrode edge (such as in FIG. 2).

BRIEF DESCRIPTION OF THE DRAWINGS

The following figures are provided to help illustrate the products, devices and methods of the application, but other variations and configurations are possible. The figures are not drawn to scale, with the size of some parts increased or decreased for clarity.

DETAILED DESCRIPTION

Cost effective commercial treatment of products, surfaces or spaces with reactive gas requires a DBD system with a reasonable service life and efficient generation of reactive gas. Experimental testing of DBD systems identified the electrode assembly as the shortest service life component of the DBD system. Extensive testing of alternative designs, materials and construction of the electrode assembly, through more than 11 iterations, has identified important elements not only for extending the service life of the electrode assembly, but also for the efficient generation of reactive gas from DBD systems which incorporate the electrode assembly. Furthermore, extensive testing of alternative designs, materials and construction of the reactive gas generator and regulator has identified important elements for efficient reactive gas generation. The present invention makes use of these testing results to provide an innovative electrode and electrode assembly. Furthermore, the present invention also includes an innovative electrode holder assembly, reactive gas generator, reactive gas generator assembly, as well as a regulator. In addition, the present invention also includes an innovative product treatment assembly.

Figure 1:
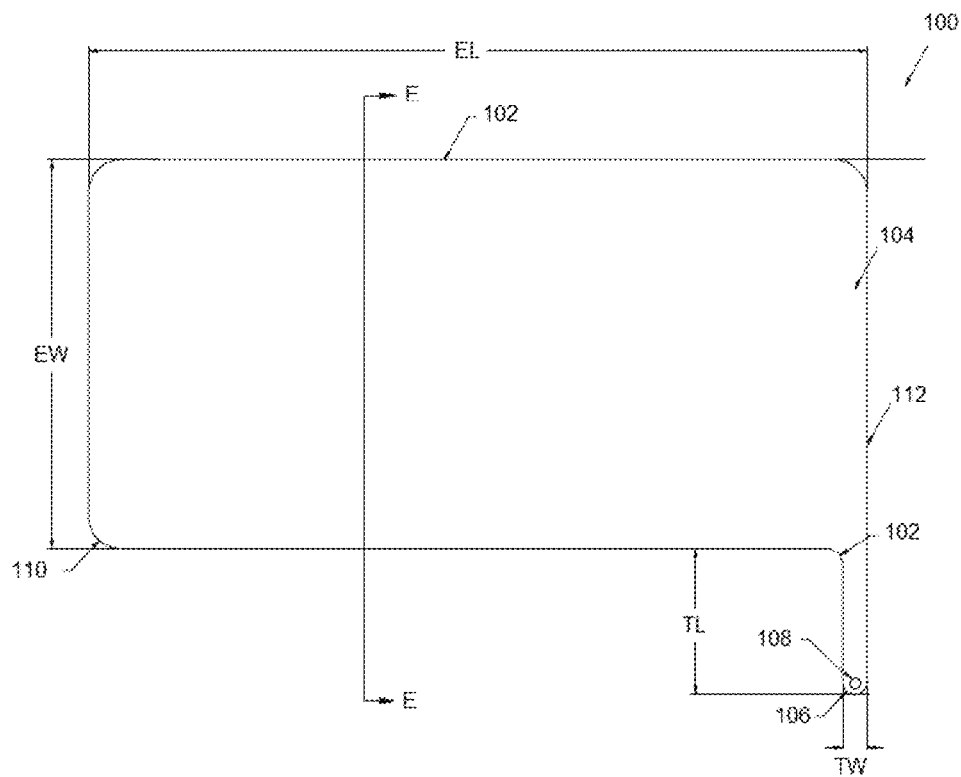
FIG. 1 is an illustration of an electrode viewed from above.

FIG. 1 is an illustration of an electrode, 100, viewed from above. The electrode has an electrode edge, 102, connecting a first electrode surface, 104, and a second electrode surface, 114 (not shown; shown in FIG. 2). The electrode also has an electrode tab, 106, which includes an electrode tab hole, 108. The curvature of the electrode edge includes the curvature of the parallel edge, 110, and the perpendicular edge, 112. In the figure ET represents the electrode thickness, EL represents the electrode length, and EW represents the electrode width. Furthermore, TL represents the tab length and TW represents the tab width.

Figure 2:
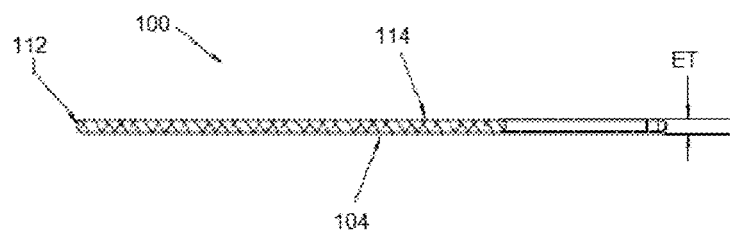
FIG. 2 is an illustration of a cross section of an electrode, viewed through cross section E-E.

FIG. 2 is an illustration of a cross section of an electrode, 100, viewed through cross section E-E. Shown are both the first electrode surface, 104, and a second electrode surface, 114, and the perpendicular edge, 112. In the figure ET represents the electrode thickness.

The electrode is formed of a metal plate with edges rounded into a semi-circle (that is, a bull-nose shape) and rounded corners. The rounding of the edges and corners is important for the longevity of the electrode assembly as it reduces the electrical field stresses to which the dielectric material is exposed. Early electrode assembly designs that had the electrode edge parallel to the electrode surfaces (that is, corners) having a curvature of only ⅜-inch radius of curvature, and made from thin 0.04-inch-thick copper had a high incidence of dielectric failure at the corners and edges, when the applied voltage exceeded 10 kV. Preferably, the radius of curvature of the electrode edge parallel to the first and second electrode surfaces is at least 2.5 cm (or at least 1 inch), including 2.5 cm to 1000 cm (or 1 inch to 400 inches), including 3, 4, 5, 10, 15, 20, 50, 100 and 500 cm (or 1.5, 2, 2.5.3, 10, 20, 50, 100, 200 and 300 inches). Preferably, the radius of curvature of the electrode edge perpendicular to the first and second electrode surfaces is at least 0.6 cm (or at least 0.25 inches), including 0.6 cm to 15 cm (or 0.25 inches to 6 inches), including 0.7, 0.8, 0.9, 1, 2, 3, 5 and 10 cm (or 0.3, 0.4, 0.5, 0.6, 0.8, 1, 2, 3 and 4 inches), although for applied voltages up to 60 kV, a radius of curvature of the electrode edge perpendicular to the first and second electrode surfaces as small as 0.1 cm (0.04 inches) may be suitable.

The electrode is made of a conductive material, such as copper or aluminum. For larger electrodes, aluminum is preferred to avoid excessive weight. Also possible would be a non-conductive core with the desired size and shape of the electrode entirely coated or plated with a conductor, such as silver or gold, to form the electrode. Furthermore, it may be desirable to avoid a perfectly flat smooth electrode surface to improve adhesion to the dielectric enclosing the first and second electrode surfaces and the electrode edge. The surface area of the electrode surfaces is chosen depending on the amount of reactive gas to be produced and the power of the reactive gas generator. Preferably, the electrode may have an electrode length EL of 30 cm to 300 cm (12 inches to 120 inches), including 35, 40, 45, 50, 65, 80, 100 and 200 cm (15, 20, 25, 30, 35, 50, 80 and 100 inches). Preferably, the electrode may have an electrode width EW of 15 cm to 150 cm (6 inches to 60 inches), including 20, 25, 30, 35, 50, 75, 100 and 125 cm (7, 8, 9, 10, 15, 20, 25, 30, 40 and 50 inches). Preferably, the electrode has an electrode thickness ET the same or similar to the radius of curvature of the electrode edge perpendicular to the first and second electrode surfaces.

Figure 3:
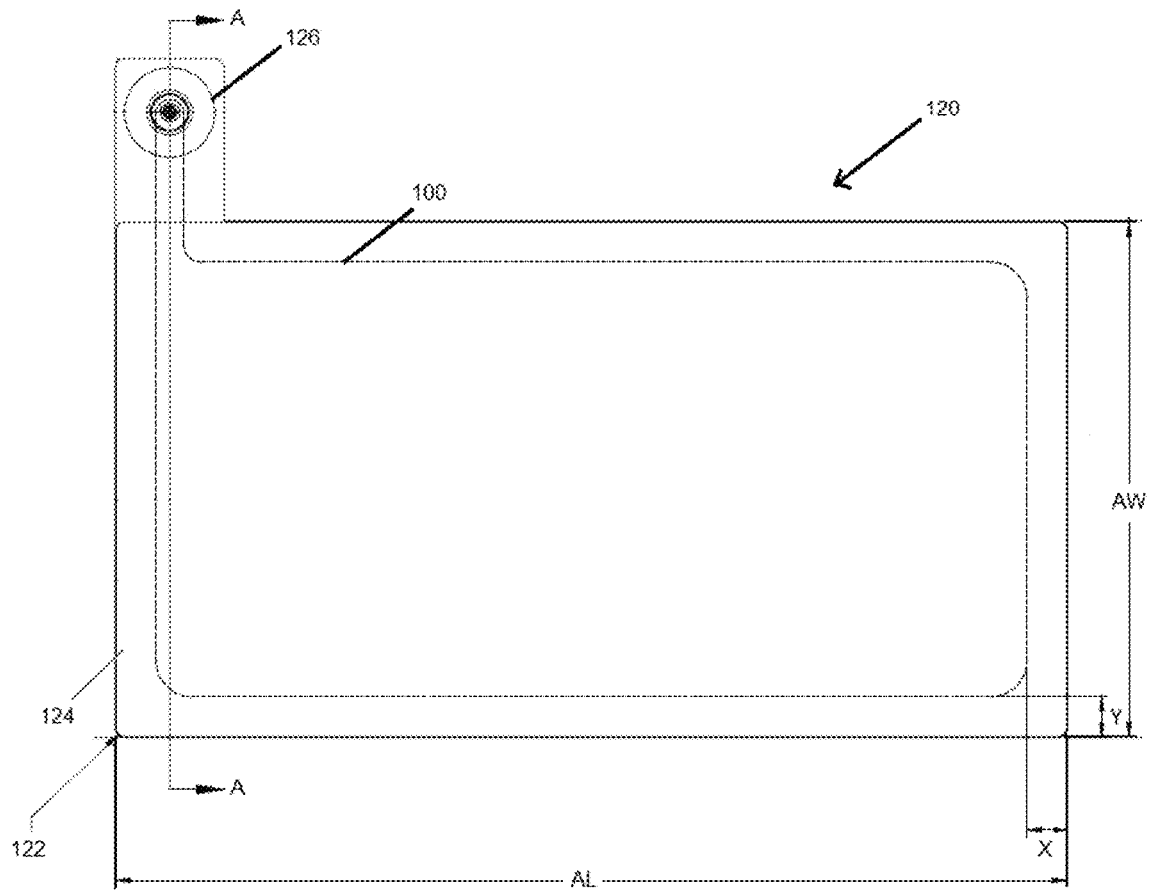
FIG. 3 is an illustration of an electrode assembly viewed from above.

FIG. 3 is an illustration of an electrode assembly, 120, viewed from above. The electrode assembly includes a conformal dielectric, 122, which encloses the first and second electrode surfaces and the electrode edge. On the first electrode surface is a first working surface, 124, with the conformal dielectric therebetween. Similarly, on the second electrode surface is a second working surface, 125 (not shown; shown in FIG. 4), with the conformal dielectric therebetween. Also illustrated is the lead assembly, 126, which includes a lead, 128 (not shown; shown in FIG. 4), in electrical contact with the electrode. In the figure AL represent the electrode assembly length and AW represents the electrode assembly width.

Figure 4:
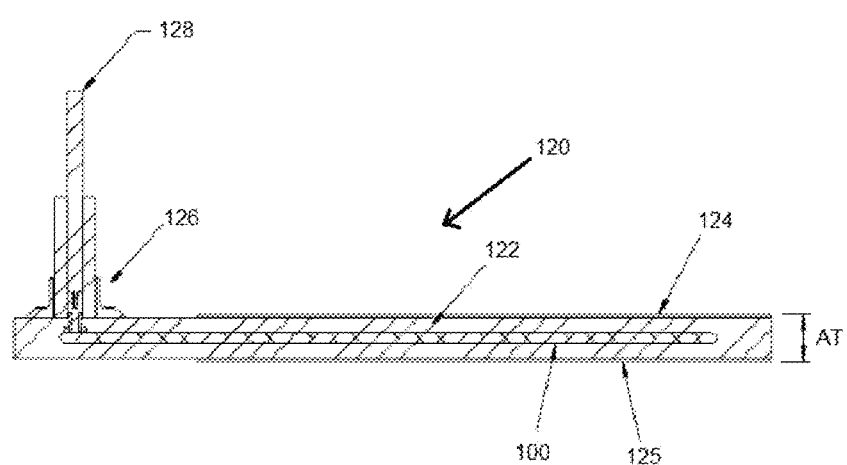
FIG. 4 is an illustration of a cross section of an electrode assembly, viewed through cross section A-A.

FIG. 4 is an illustration of a cross section of an electrode assembly, 120, viewed through cross section A-A. Shown are the electrode, 100, the conformal dielectric, 122, the first working surface, 124, and the second working surface, 125.

Also shown are the lead assembly, 126, including the lead, 128. In the figure AT represents the electrode assembly thickness.

It is important that the dielectric is conformal to the electrode, as defects such a gas bubbles at the dielectric-electrode interface will significantly reduce the service life of the electrode assembly. This was determined by testing designs that contained incidental defects or bubbles, which were the location of failure of the dielectric material. One way to accomplish this is by sealing the electrode into a polymerizable liquid dielectric material, such as an epoxy, by vacuum casting of the liquid into a mold, with the electrode suspending in the center of the mold. Similarly, a polymer could be injection molded around the electrode to form the electrode assembly. Alternatively, a thin dielectric (such as 8690 STATICIDE® acrylic conformal coating) may be coated onto the electrode surface to form a conformal coating, and then the remaining thickness of dielectric, such as an epoxy glass composite (for example, an EPOXYGLAS G10 or FR4, such as that available from ACCULAM) is formed as a frame, with the conformally coated electrode sealed into the frame, using for example an epoxy resin (such as RESINLABO EP750 CLEAR food grade two part unfilled epoxy structural adhesive). Dimensional stability and heat resistance of the dielectric is important, as well as the strength of adhesion between dielectric materials including any adhesive or glue, which was determined when earlier versions were prepared from polypropylene and silicone calk. Resistance to oxidation from the reactive gas and resistance to ultraviolet (UV) radiation produced by the HVCP is also important, especially on the working surfaces of the electrode assembly. The thickness of the dielectric should be the same on both sides of the electrode, and extend beyond the electrode forming a perimeter around the metal conductor; in FIG. 3 the perimeter has a length X along the assembly width AW, and a width Y along the assembly length AL. The thickness of the dielectric depends on the voltage used for the electrodes, and the variability of the voltage over the desired services life: Preferably, the dielectric has a thickness which provide a breakdown voltage corresponding to at least 110% of the voltage used for the electrode, more preferably a breakdown voltage corresponding to at least 130% of the voltage used for the electrode, and most a breakdown voltage corresponding to at least 150% of the voltage used for the electrode. When the voltage of the electrode is at least 60 kV, preferably X is at least 1.5 cm (or at least 0.625 inches), and Y is at least 2.8 cm (or at least 1.125 inches). When the voltage of the electrode is at least 60 kV, preferably the dielectric has a thickness of at least 0.9 cm (at least 3/8 of an inch), both above and below the electrode. The upper limit of X, Y and the thickness of the dielectric above and below the electrode, is limited by the difficulty of handling the electrode assembly due to its weight and physical dimensions. The electrode assemblies are identical regardless of whether they are used as hot electrode assemblies or ground electrode assemblies.

Preferably, the first and second working surfaces of the electrode assembly comprise glass. By studying several different electrode assembly designs, it was determined that epoxy material could not withstand the long-term effects of UV radiation and oxidation from the reactive gasses. It was also determined that the amount of reactive gas produced was affected by the selection of materials for the working surfaces. As compared to mica, glass produced about twice as much reactive gas. Particularly preferred is an alkali-aluminosilicate thin sheet glass that has been subject to ion exchange to increase toughness and resistance to damage, such as GORILLA® glass 3 with NATIVE DAMAGE RESISTANCE™ (Corning). Preferably the glass has a thickness of about 2 mm and has a beveled edge. Because the glass has a coefficient of expansion different from epoxy, it should be attached to the surface with an elastomeric adhesive, such as a platinum cured two-part silicone resin (for example, DOW CORNING® 3-4207 dielectric tough gel). Each electrode assembly is handed (that is, they have a non-superimposable mirror image), and may be identified with a relative designation of "right hand" or "left hand".

The lead assembly and attachment of the lead to the electrode tab can have a significant effect on electrode assembly lifetime. Preferably, the lead is soldered to a metal screw (such as brass), which is screwed into the electrode tab hole. The metal parts should be cemented in place with epoxy adhesive and further protected by, for example an epoxy glass composite tube filled with epoxy adhesive, and finally covered with a polyvinylidene fluoride (PVFD) tube, all of which is further sealed with epoxy adhesive. Alternatively, the wire may be attached to the electrode using a multilam style plug and socket. The socket has a threaded end that attaches to the metal electrode. The socket is protected by a molded epoxy tube which is vacuum cast with the dielectric. The plug is soldered to the end of the wire connector that has a molded silicon shroud that is attached to the wire insulation above the plug. The shroud and plug are coated with a dielectric silicone grease and are inserted into the tube protecting the socket, and the plug is engaged in the socket. The grease provides an air tight high voltage connection that eliminated air and prevent coronal discharges to the socket and plug. This removable plug assembly allows any right or left handed electrode to be used in any slot in the electrode holder assembly.

It is desirable for an electrode assembly to have a service life of at least 20 hours, or at least 30 hours, at a voltage of 10 kV, more preferably a voltage of 30 kV, and most preferably a voltage of 60 kV. In the most desirable forms, the electrode assembly will have a service life of at least 300 hours at a voltage of 60 kV, alternatively, the electrode assembly will have a service life of at least 20 hours, or at least 30 hours, at a voltage of 76 kV.

Figure 5:
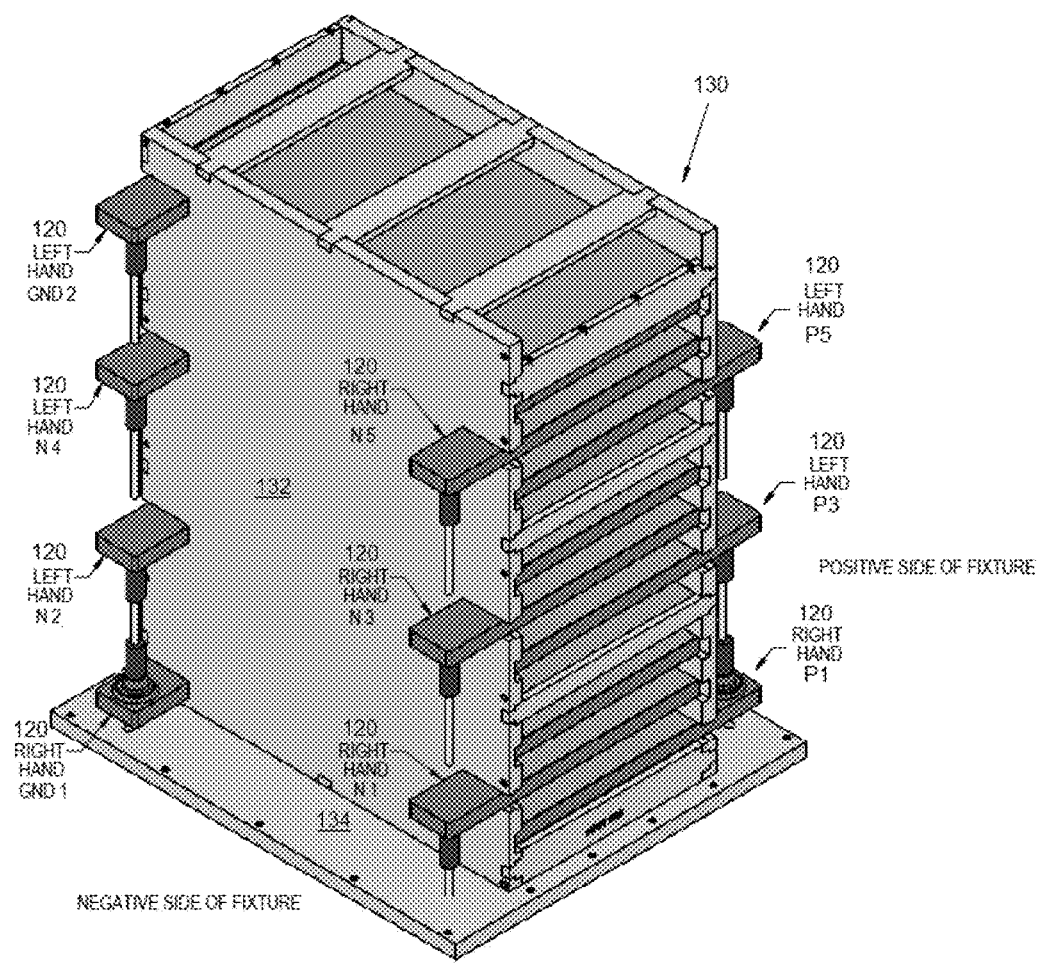
FIG. 5 is an illustration of an electrode holder assembly.

FIG. 5 is an illustration of an electrode holder assembly, 130. The electrode holder assembly includes an electrode holder frame, 132, and an electrode holder base, 134. Electrode assemblies, 120, each fit into slots present in the electrode holder frame, with the electrode tab of each electrode and the lead assembly of each electrode assembly protruding outside of the electrode holder frame, to allow for electrical connection to a high voltage power source. The figure also illustrates a convenient way to orient and organize the electrode assemblies within the electrode holder assembly to simplify connecting a split pole high voltage power source. One side of the electrode holder assembly may be identified with the relative designation of the "positive side of fixture" and the opposite side identified with a relative designation of the "negative side of fixture", with the designation of "P" and "N" shown in the figure for polarity of each hot electrode (the electrode are also numbered in the figure). By alternating the lead assemblies of adjacent electrodes on each side of the electrode holder assembly, both working surfaces of each electrode assembly will participate in forming a HVCP and produce reactive gas. Furthermore, all leads present on the same side of the electrode holder assembly are connected to the same polarity of high voltage power. Lastly, the electrodes at the top and bottom of the electrode holder assembly are connected to ground. The presence of the ground electrodes protects against electrical discharge outside of the electrode holder assembly from charge buildup on the non-active side of the electrode assemblies at each end. In the figure, two electrodes are not visible—"RIGHT HAND P2" and "RIGHT HAND P4". As illustrated, the gap between an end hot electrode and the adjacent ground electrode is blocked to further inhibit electrical discharge outside of the electrode holder assembly and prevent air or the working gas from flowing between the ground electrode assemblies and the adjacent hot electrode assemblies.

Figure 6:
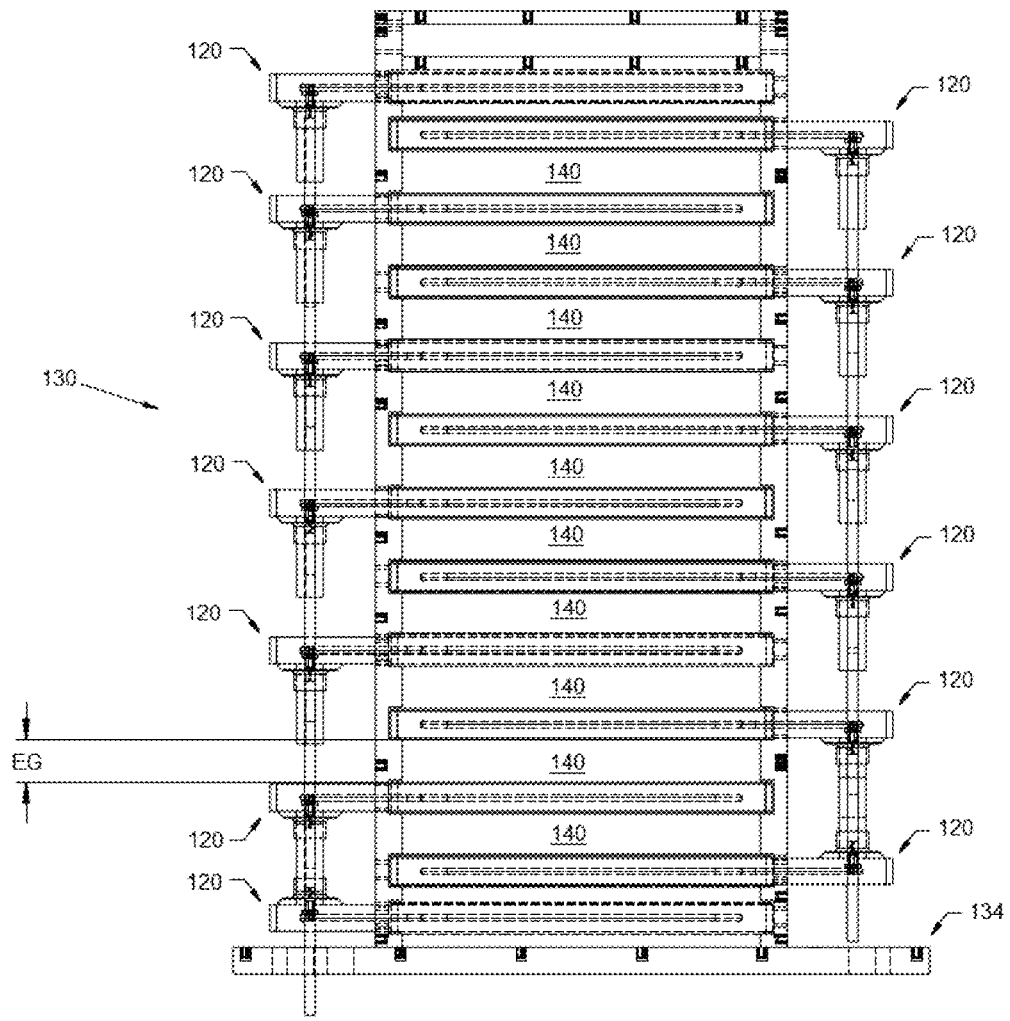
FIG. 6 is an illustration of a cut-away view of an electrode holder assembly.

FIG. 6 is an illustration of a cut-away view of an electrode holder assembly, 130. This figure is used to show the active electrode gap, 140, between adjacent pairs of electrode assemblies, 120. In the figure EG means electrode gap size. Each active electrode gap will produce an HVCP and reactive gas. The electrode gap size is the same between each pair of hot electrode assemblies. Preferably, the gap between the ground electrode assemblies and the adjacent hot electrode assembly is smaller than the electrode gap size. The specific electrode gap is selected based on the voltage at which the reactive gas generator will be operated, with an electrode gap EG of 1.25 cm to 6.25 (0.5 to 2.5 inches). including 1.5, 2, 2.5, 3, 3.5, 4, 4.5, 5 and 6 (0.75, 1, 1.25, 1.5, 1.75, 2, and 2.25 inches) being preferred. The number of electrode assemblies is selected based on the power at which the reactive gas generator will be operated, and is preferably an odd number of hot electrode assemblies, such as 3, 5, 7, 9, 11, 13, 15, 17, 19, 21 and 23. Even numbers of hot electrode assemblies are also possible. Typically, only 2 ground electrode assemblies are used, one on each end of the electrode holder assembly.

Preferably, the electrode holder includes an insulating inorganic material, such as mica, a mica composite, glass, a glass composite, or ceramic or a ceramic composite. Several experiments using epoxy glass composite as the holder material demonstrated that it was unable to provide a long service life due to the effects of UV radiation and oxidation by reactive gas.

Figure 7:
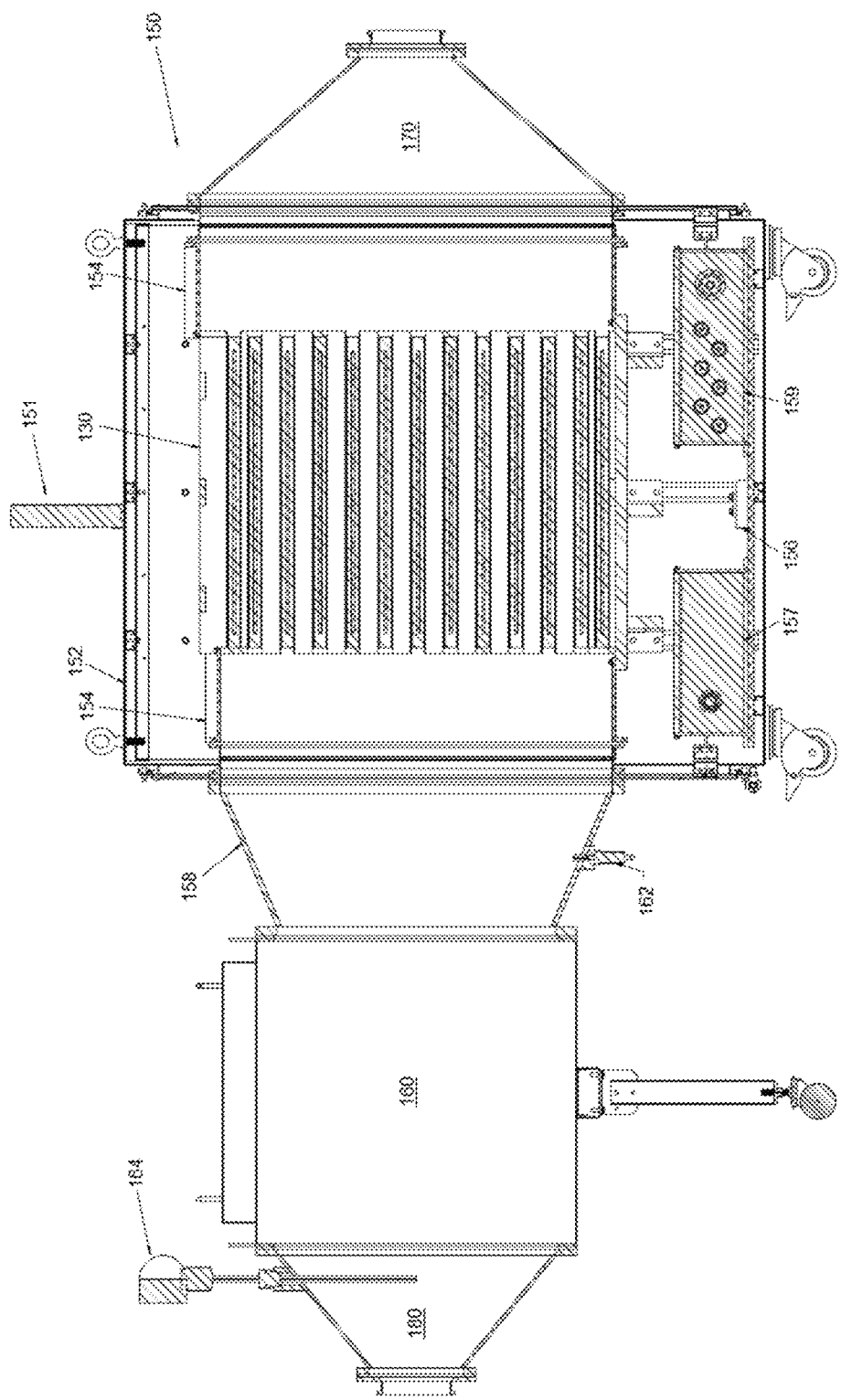
FIG. 7 is an illustration of a reactive gas generator assembly, with a cut-away view of the reactive gas generator to show internal structures.

FIG. 7 is an illustration of a reactive gas generator assembly, with a cut-away view of the reactive gas generator, 150, to show internal details. The reactive gas generator assembly includes two main parts, a reactive gas generator, 150, and a filter assembly, 160, connected by a connector duct, 158. Also present are an intake duct, 180, where the working gas enters the reactive gas generator assembly, and an exhaust duct, 170, where reactive gas exits the reactive gas generator assembly.

The reactive gas generator, 150, includes an electrode holder assembly, 130, with two internal ducts, 154 and 154, fluidly connecting the electrode holder assembly to the intake duct and the exhaust duct. The reactive gas generator also includes a first power splitter, 157, a second power splitter, 159, and a return ground assembly, 156, for providing power and grounding to the electrodes (the electrical connections to the electrode assemblies in the electrode holder assembly are not shown). A generator cabinet, 152, holds the different parts of the reactive gas generator together. Also shown in the figure are a status light, 151, for notifying users when power is being applied to the electrode assemblies or it is safe to open the generator cabinet. Lastly, a dew point sensor, 162, for measure the dew point of the working gas, and a mass airflow sensor, 164, for measuring the amount of working gas entering the reactive gas generator are also shown in the figure.

Figure 8:
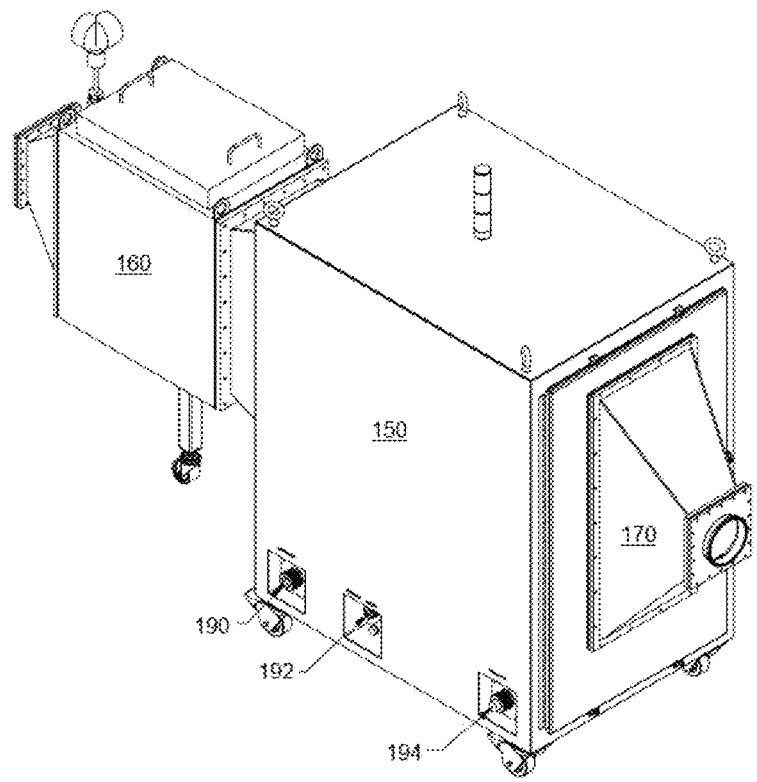
FIG. 8 is an illustration of a side view of a reactive gas generator assembly.

FIG. 8 is an illustration of a side view of a reactive gas generator assembly. Illustrated are a first power input, 190, for providing power to the first power splitter, a second power input, 194, for providing power to the second power splitter, and a ground return, 192, for electrically connecting the return ground assembly to ground.

Figure 9:
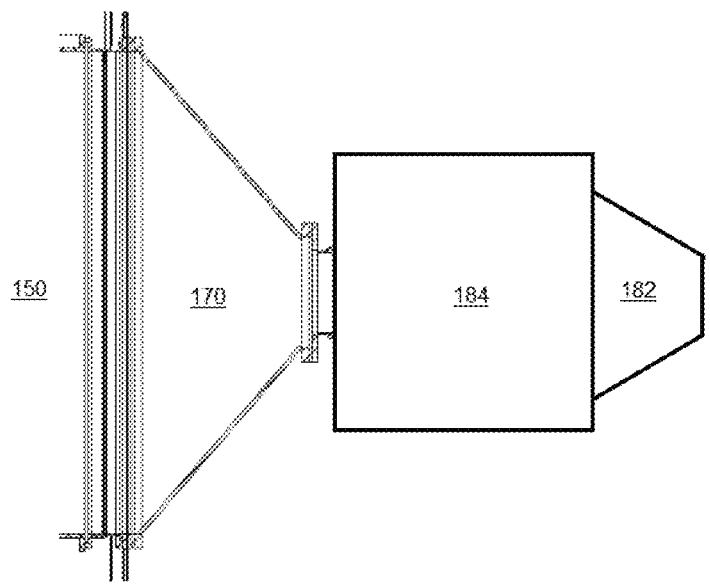
FIG. 9 is an illustration of a partial view of a reactive gas generator assembly showing an optional blower and blower exhaust.

FIG. 9 is an illustration of a partial view of a reactive gas generator assembly showing an optional blower, 184, and blower exhaust, 182. The optional blower may be part of the reactive gas generator assembly when it is used in a room, for sterilizing the surfaces within the room (such as an operating theater, a room contaminated with microorganisms such viruses or bacteria including a cruise ship cabin, or space contaminated with a toxin including chemical warfare agents; and including killing viruses or rendering them uninfective, for example norovirus, measles, rotovirus, ebola, influenza, African swine fever virus, avian viruses, Middle East respiratory syndrome coronavirus, SARS; and rendering prions un-infective), or to provide a mobile station for producing and transporting reactive gas.

Figure 10:
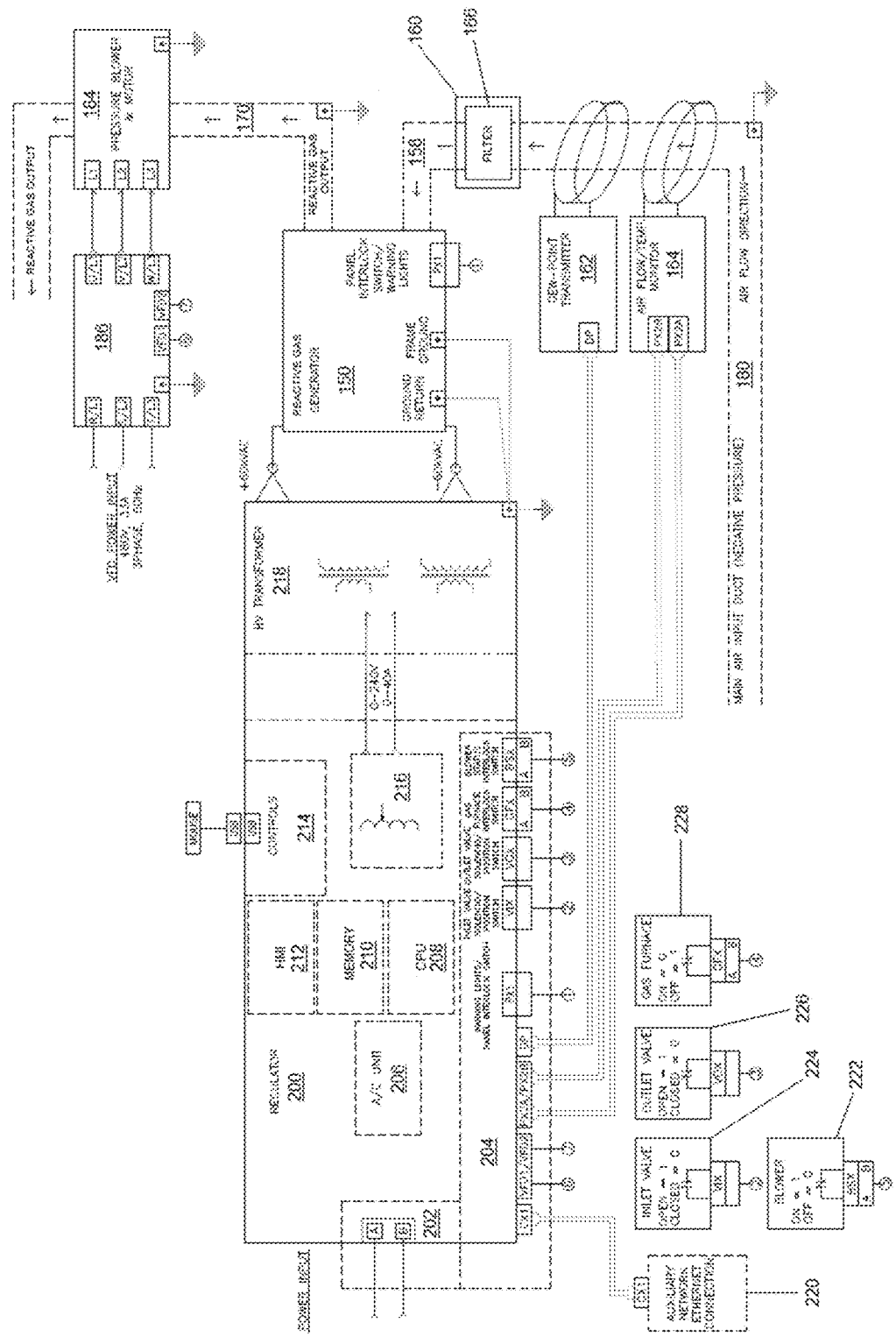
FIG. 10 is a schematic of a reactive gas generator assembly and a regulator.

FIG. 10 is a schematic of a reactive gas generator assembly, and regulator, 200. The regulator, 200, controls the reactive gas generator, 150. Air (or another working gas) enters the reactive gas generator assembly through an intake duct, 180, allowing sensing by the dew point sensor, 162, and mass airflow sensor, 164. The dew point sensor and the mass airflow sensor may be position either before or after the working gas passes through the filter assembly, 160 and the filter, 166 (such as a HEPA filter). Furthermore, the mass airflow sensor may also measure the temperature of the working gas, or a separate temperature sensor may be used. From the filter assembly the working gas passes through the connector duct, 158, and into the reactive gas generator, 150, where reactive gas is produced from the working gas and an HVCP. The reactive gas then passes into the exhaust duct, 170, pulled along by a blower, 184, which is controlled by the blower controller, 186. The reactive gas is then delivered to the desired location for treating a product, surface or room.

As illustrated in FIG. 10, the regulator, 200, includes a power input, 202, and input/output interface, 204, a (CPU), 208, such as a programmable logic controller (PLC), controls, 214, for allowing control of the regulator by a human user, a computer readable memory, 210, and a human user interface, 212, such as a HMI display screen, all of which are in electrical communication. Also in electrical communication is a variable transformer, 216, which allows a human user (with the assistance of the CPU and any software and/or data present on the computer readable memory) to control the voltage going to a high voltage transformer, 218, which in turn provides power to the reactive gas generator. As illustrated, the high voltage transformer is a step-up transformer which is powered by household power derived from a split phase transformer (also known as a single phase three wire transformer), but other types of high voltage transformers may be used. The voltage supplied to the reactive gas generator may vary depending on the high voltage transformer, but preferably the voltage difference between the two poles ranges from 30 kV to 120 kV (that is, each pole supplying 15 kV to 60 kV, as alternating current (AC) with a 180° phase difference). An air conditioning unit, 206, is included to remove waste heat generating within the regulator. Data collected through the input/output interface from various sensors (such as a blower status indictor, 222, an inlet valve indicator, 224, an outlet valve indicator, 226, and a gas furnace indicator, 228) may be displayed to the user and used to prevent operation of the reactive gas generator when operation would be unsafe. Such information may also be used to control the operation of the status light, 151 (shown in FIG. 7, but not in FIG. 10), which may also be in electrical communication with the regulator or the reactive gas generator. Also through a connection in the input/output interface, the optional blower may be controlled through the blower controller. Lastly, a network connection, 220, may be used to send or receive information to/form the regulator, or for remote control or programming of the regulator.

In a split phase transformer, the (input) primary winding on the transformer is single phase, the (output) secondary winding is center-tapped, and the center tap is connected to a grounded neutral. Either end to the center of the transformer has half the voltage of end-to-end. The advantage of using this type of transformer is that it reduces the wire conductor size as well as reduces the thickness of the wire insulation going to the electrode, as the wire only has to carry half the voltage. This is necessary as the electrodes are stacked in the electrode holder assembly in such a way as to require a tight bend radius on the wire connectors. For example, one electrode assembly may be supplied with +40 kV (AC), with the adjacent electrode assembly supplied with −40 kV (AC), giving a voltage difference between the electrode assemblies of 80 kV (AC).

In order to most efficiently produce reactive gas for a given power consumption, the voltage is selected based on the electrode gap size. More specifically, the larger the electrode gap size, the greater the voltage necessary to produce the HVCP (referred to as the light off voltage). Efficient reactive gas production occurs when the reactive gas generator is operated at between 25% to 30% above the light off voltage. Higher voltages do not produce more reactive gas efficiently. For example, a 2.5 cm (1 inch) electrode gap will have a light off voltage of 48 kV, and will most efficiently produce reactive gas when operated at 60 to 65 kV. In another example, a 3.75 cm (1.5 inch) electrode gap will have a light off voltage of 72 kV, and will most efficiently produce reactive gas when operated at 90 to 95 kV. Also, for otherwise identical devices, a 1.25 cm (0.5 inch) increase in the electrode gap size will result in about a doubling of the power of the reactive gas generator, when operated at between 25% to 30% of the light off voltage. Regulators providing high voltage with a power output of 1 kW, 8 kW and 30 kW are preferred.

Figure 11:
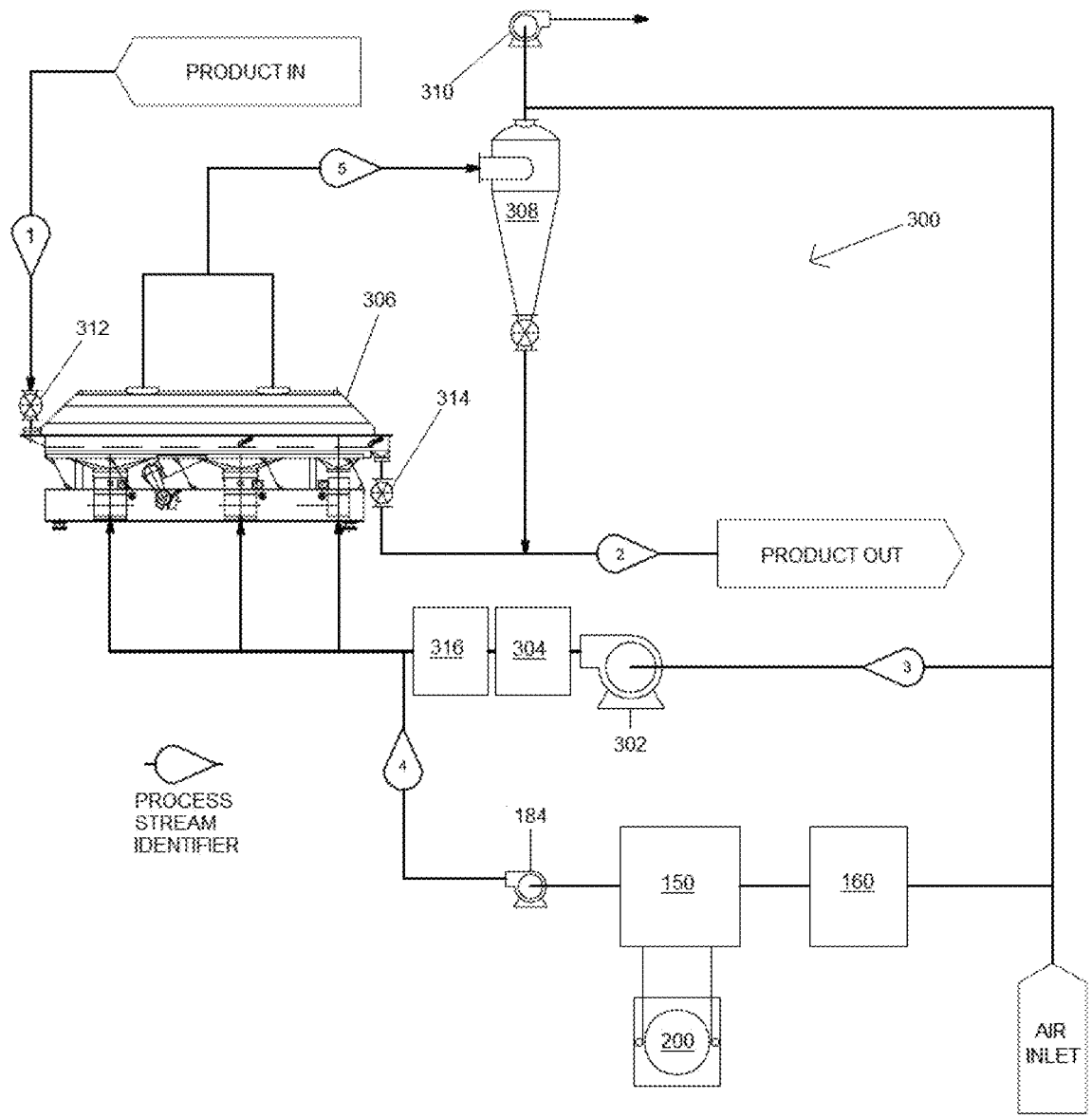
FIG. 11 is a schematic of a product treatment assembly.

FIG. 11 is a schematic of a product treatment assembly, 300. This product treatment assembly may be a grain dryer modified to also allow for treatment of a product with reactive gas. This figure includes process stream identifiers to aid in understanding the flow of product (such as grain, fruit, seeds, nuts, ground forms thereof, as well as any product that could be moved through a fluidized bed). A working gas, such as air, enters through a filter assembly, 160, and into a reactive gas generator, 150, electrically connected to a regulator, 200. The reactive gas generator then produces reactive gas which flows through a blower, 184, and into process stream 4, prior to entering a fluid bed, 306. Air (or another gas) enters through a fluid bed blower, 302. Since the product treatment assembly may also be used to dry product (such as grain), a fluid bed heater, 304, may also be present, but typically it is not turned on during treatment of product with reactive gas. The air then enters a fluid bed filter, 316, to remove dust or other particulates, and then enters process stream 4. In an alternative embodiment, the reactive gas may be mixed with the air in process stream 3 before the air enters the fluid bed blower.

The reactive gas enters the fluid bed, 306. Product also enters the fluid bed at the product inlet, 312, passes through the fluid bed, 306, and then exits at the product outlet, 314, where it is collected as process stream 2. The product is exposed to, and treated by, the reactive gas in the fluid bed. Reactive gas then travels to optional entrained product separator, 308, for removal of any entrained product, and then exits the assembly through the exhaust blower, 310. Although illustrated with a fluid bed type grain dryer, other types of continuous flow dryers could be used in place of the fluid bed, such as those described in "Improving Energy Efficiency in Grain Drying" ENCON2.3 Fact Sheet (December 2012) (available at blogs.extension.org/encon1/files/2012/12/FS_FlowDryers.pd). Also possible is to use a perforated belt conveyor where articles are placed on the conveyor and passed through a tunnel where spaced nozzles pass the reactive gas across the article. Optionally, the reactive gas may be fed back into the assembly as the working gas.

Figure 12:
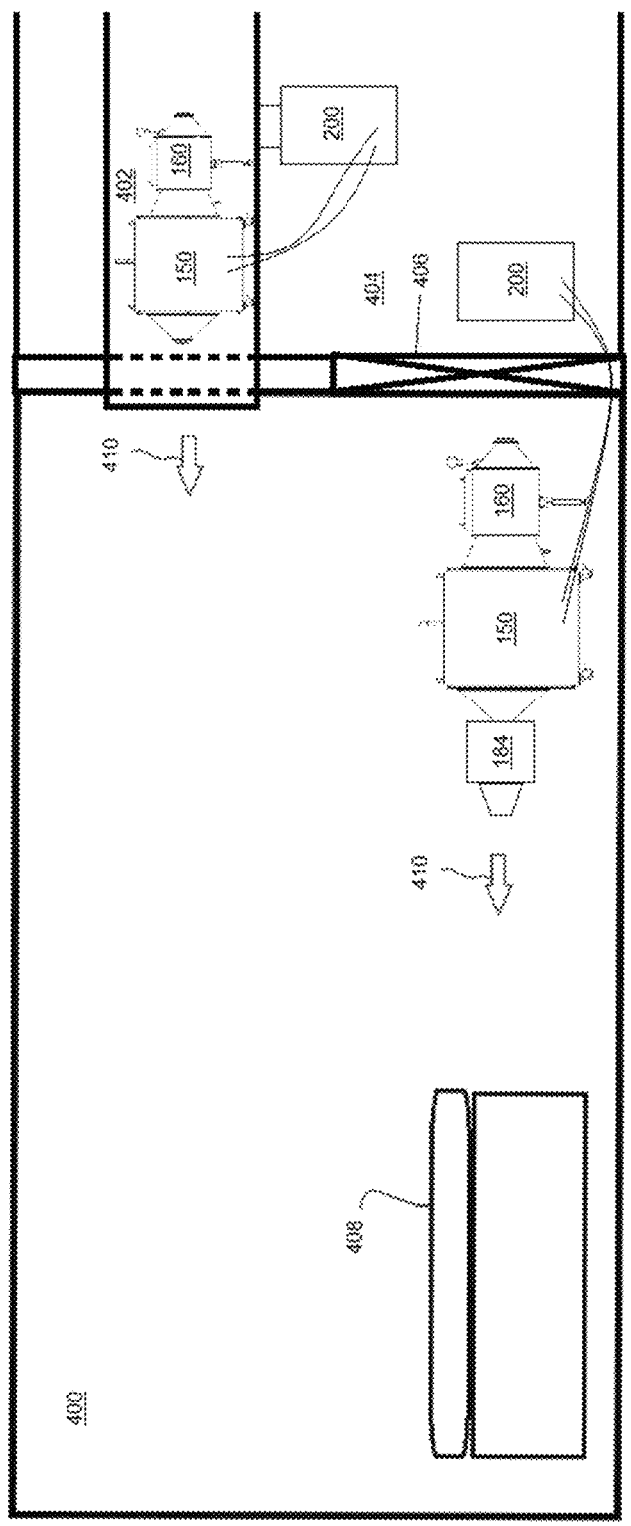
FIG. 12 is an illustration of two configurations for treating a room or other enclosed space with reactive gas.

FIG. 12 is an illustration of two configurations for treating a room, 400, or other enclosed space with reactive gas, 410. In a first configuration, the reactive gas generator assembly including the reactive gas generator, 150, is placed within a room. The regulator, 200, electrically connected to the reactive gas generator is placed outside the room so as to avoid exposing it to the reactive gas. In the figure the regulator is place in a hallway, 404, separated from the room by a door, 406. The reactive gas is blown through a blower, 184, and into the room so that it may treat or sterilize room surfaces, 408. In an alternative configuration for treating a room, the reactive gas generator assembly including the reactive gas generator, is present in the air handling duct system, 402, which is used to provide heat and/or air conditioning to the room. In this way, no blower is needed as part of the reactive gas generator assembly as the blower used in the air handling duct system may be used to blow the reactive gas into the room. When used in this way, all the components of the reactive gas generator assembly should be selected for resistance to damage from the reactive gas.

Examples

Several different electrode assemblies were tested. Each subsequent electrode assembly was designed to prevent the failure mechanism which had ended the use of the prior electrode assembly design. As the failure mechanisms which appeared most quickly were eliminated, and electrode assembly service life increased, higher voltages and longer service times revealed new failure mechanisms, which were each addressed in turn. Several different electrode assemblies are described in Tables 1-3, below. Not all electrode assemblies tested are included in the tables. Version 11 has been constructed, but testing has not been completed.

TABLE 1

Electrode Development (versions 1-4)

| | Electrode Assembly Version | | | |
|---|---|---|---|---|
| | 1 | 2 | 3 | 4 |
| Voltage Range kV | 15 to 50 | 15 to 50 | 15 to 50 | 15 to 50 |
| Electrode Gap Size | ¼" to 1" | ¼" to 1" | ¼" to 1" | ¼" |
| Radius on Electrode Corners | ⅜" | ⅜" | ⅜" | ⅜" |

TABLE 1-continued

Electrode Development (versions 1-4)

| | Electrode Assembly Version | | | |
|---|---|---|---|---|
| | 1 | 2 | 3 | 4 |
| Dielectric Material Thickness | ⅛" | ⅛" Edge Chamfered at 45°. | 3/32" 1.1 mm display glass placed on both top and bottom surface. | ⅛" |
| Dielectric Material Edge distance to Electrode | ⅜" | ⅜" | ⅜" | ⅜" |
| Electrode Thickness | 0.04" | 0.04 | 0.04 | 0.04 |
| Radius on Electrode edge | No | Yes | Yes | Yes |
| Construction Method | Metal electrode sandwiched between dielectric material and sealed with silicone caulk along the perimeter of electrode. | Metal electrode sandwiched between dielectric material and sealed with silicone calk along the perimeter. New plug wire soldered and sealed to electrode. | Metal electrode sandwiched between the dielectric material and sealed together with silicone caulk. Glass applied on dielectric and glued together with silicone caulk. | Metal Electrode sandwiched between dielectric material. Hot weld bead of polypropylene around the perimeter. |
| Failure Mode | Failure along the bond line between the caulk and the polypropylene on electrode assembly corners. Failure at the wire connection to the electrode. | Failure on the corner along the bond line. Noticed Polypropylene surface of the electrode assembly becoming dull. | Failure on the electrode assembly corner along the bond line. Glass subject to fracture with mechanical handling. | Dielectric not dimensionally stable, causing a weak weld. |
| Mean Run Time to Failure | 3 to 5 hours at less than 60 kV. | 1 to 2 hours at less than 60 kV. | 1 to 2 hours at less than 60 kV. | 0 hours. |

TABLE 2

Electrode Development (versions 5-8)

| | Electrode Assembly Version | | | |
|---|---|---|---|---|
| | 5 | 6 | 7 | 8 |
| Voltage Range kV | 25 to 80 | 25 to 80 | 40 to 100 | 40 to 100 |
| Electrode Gap Size | ½" to 1.5" | ½" to 1.5" | 1" to 2" | 1" to 2" |
| Radius on Electrode Corners | ⅜" | 1" | 1" | 1" |
| Dielectric Material Thickness | ¼" | 11/32" | ⅜" | ⅜" |
| Dielectric Material Edge distance to Electrode | 1 1/16" in flow path ½" on sides against electrode holder assembly. | 1⅛" in flow path ⅞" on sides against electrode holder assembly. | 1⅛" | 1⅛" |
| Electrode Thickness | 0.04 | 0.04 | 0.04 | 0.04 |
| Radius on Electrode edge | Yes | Yes | Yes | Yes |
| Construction Method | Bond line above electrode, sealed with epoxy. Electrode assembly working surface covered with 1.1 mm glass. | Bond line above the electrode, sealed with epoxy. Moved tab to side of electrode holder assembly. Electrode assembly working surface covered with 2 mm GORILLA ® glass. | Bond line above electrode, sealed with epoxy. Increase length of tab. Used conformal coating on the electrode. Electrode assembly working surface covered with 2 mm GORILLA ® glass. | Two bond lines, both above the electrode on each side, mica composite sealed with epoxy. Conformal coating on the electrode. |

TABLE 2-continued

Electrode Development (versions 5-8)

| | Electrode Assembly Version | | | |
|---|---|---|---|---|
| | 5 | 6 | 7 | 8 |
| Failure Mode | Failure midline to the electrode on the corner. Failure at plug connection to electrode. Failure through the glass. | Failure midline to the electrode on the side against the electrode holder assembly. | Failure midline to the electrode on the side against the electrode holder assembly. Infrequent failure of wire connection to electrode. | Weakness at the bond line. No defined failure, but arcing from the edge of the electrode assembly. |
| Mean Run Time to Failure | 10-15 hours at less than 60 kV. | 20-30 hours up to 60 kV. | At 60 kV no failures (300+ hours). 20 to 30 hours at 76 kV. | Operated for 3 hours at 60 kV. Testing ended due to arcing. |

TABLE 3

Electrode Development (versions 9-11)

| | Electrode Assembly Version | | |
|---|---|---|---|
| | 9 | 10 | 11 |
| Voltage Range kV | 40 to 100 | 40 to 100 | 40 to 100 |
| Electrode Gap Size | 1" to 2" | 1" to 2" | 1" to 2" |
| Radius on Electrode Corners | 1" | 1" | 1" |
| Dielectric Material Thickness | 3/8" | 3/8" | 3/8" |
| Dielectric Material Edge distance to Electrode | 1 1/8" | 1 1/8" | 1 1/8" |
| Electrode Thickness | 0.04 | 0.04 | 1/4" |
| Radius on Electrode edge | Yes | Yes | Yes |
| Construction Method | Version 7 construction with new design for sealing wire to electrode featuring potting the wire with epoxy inside dielectric tube sealed to the electrode assembly, Conformal coating on the electrode. | Version 9 construction with conformal coating on the electrode and then the edge of the electrode assembly covered with mica tape that was attached with epoxy onto the electrode assembly. | Version 9 construction with electrode coated with conformal coating on the electrode. Edge of electrode with full bull-nose 1/4" radius. |
| Failure Mode | Failure midline to the electrode assembly on the side against the electrode holder assembly. | Failure midline to the electrode assembly on the side against the electrode holder assembly. | |
| Mean Run Time to Failure | 20-30 hours at 76 kV. | 20-30 hours at 76 kV. | |

What is claimed is:

1. An electrode assembly, comprising:
   (a) a conductive electrode, having
      (i) a first electrode surface,
      (ii) a second electrode surface, opposite the first electrode surface,
      (iii) an electrode edge, connecting the first and second electrode surfaces, and
      (iv) an electrode tab, for making an electrical connection to the electrode,
   (b) a dielectric, enclosing the first and second electrode surfaces and the electrode edge,
   (c) a first working surface, on the first electrode surface, wherein the dielectric is present between the first working surface and the first electrode surface, AD
   (d) a second working surface, on the second electrode surface, wherein the dielectric is present between the second working surface and the second electrode surface
   wherein the dielectric is conformal with the first electrode surface, the second electrode surface and the electrode edge, with no gas bubble defects at dielectric-electrode interfaces,
   the first working surface comprises glass, and the second working surface comprises glass, and
   the glass has a thickness of at least 1 mm.

2. The electrode assembly of claim 1, wherein the first and second electrode surfaces are planar.

3. The electrode assembly of claim 2, wherein a radius of curvature of the electrode edge parallel to the first and second electrode surfaces is at least 1 inch.

4. The electrode assembly of claim 3, wherein a radius of curvature of the electrode edge perpendicular to the first and second electrode surfaces is at least 0.25 inches.

5. An electrode holder assembly, comprising:
   (1) an electrode holder base,
   (2) an electrode holder frame, on the electrode holder base, and
   (3) a plurality of electrode assemblies, in the electrode holder frame, wherein the electrode holder base and the electrode holder frame comprise an insulating inorganic material,
   an electrode gap size between each of the plurality of electrode assemblies is at least 0.5 inches, and
   each of the plurality of electrode assemblies comprises the electrode assembly of claim 1.

6. The electrode holder assembly of claim 5, wherein the electrode gap size is 0.5 inches to 2.5 Inches.

7. A reactive gas generator, comprising:
   (I) a generator cabinet,
   (II) the electrode holder assembly of claim 5, in the generator cabinet, (III) an intake duct, on a first side of the cabinet, and (IV) an exhaust duct, on a second side of the cabinet, opposite the first side of the cabinet.

8. The reactive gas generator of claim 7, further comprising
(VI) a first power splitter, in the generator cabinet, electrically connected to a first portion of the plurality of electrode assemblies, and
(VII) a second power splitter, in the generator cabinet, electrically connected to a second portion of the plurality of electrode assemblies.

9. The reactive gas generator of claim 7, further comprising
(IX) a blower, attached to the exhausted duct, and
(X) a blower exhaust, attached to the blower.

10. An electrode holder assembly, comprising:
(1) an electrode holder base,
(2) an electrode holder frame, on the electrode holder base, and
(3) a plurality of the electrodes assemblies, in the electrode holder frame, each of the plurality of electrode assemblies comprising the electrode assembly of claim 4,
wherein the electrode holder base and the electrode holder frame comprise an insulating inorganic material, and
an electrode gap size between each of the plurality of electrode assemblies is at least 0.5 inches.

11. A reactive gas generator, comprising:
(I) a generator cabinet,
(II) the electrode holder assembly of claim 10, in the generator cabinet,
(III) an intake duct, on a first side of the cabinet, and
(IV) an exhaust duct, on a second side of the cabinet, opposite the first side of the cabinet.

12. A reactive gas generator assembly, comprising:
(A) the reactive gas generator of claim 7, and
(B) a regulator, electrically connected to the reactive gas generator,
wherein the regulator comprises a high voltage transformer, for providing high voltage to the reactive gas generator.

13. A product treatment assembly, comprising:
a fluid bed, and
the reactive gas generator assembly of claim 7, connected to supply reactive gas generated by the reactive gas generator to air entering the fluid bed.

14. A method of removing mycotoxins from a product or sterilizing a product, comprising
generating reactive gas with the product treatment assembly of claim 3; and
contacting the product with the reactive gas.

15. A method of killing viruses on surfaces in a room, comprising:
generating reactive gas with the reactive gas generator of claim 9, and
contacting surfaces in the room with the reactive gas.

16. The method of claim 15, wherein the room is a cruise ship cabin.

17. The method of claim 16, wherein the viruses comprise norovirus.

18. An electrode assembly, comprising:
(a) a conductive electrode, having
(i) a first electrode surface,
(ii) a second electrode surface, opposite the first electrode surface,
(iii) an electrode edge, connecting the first and second electrode surfaces, and
(iv) an electrode tab, for making an electrical connection to the electrode,
(b) a dielectric, enclosing the first and second electrode surfaces and the electrode edge,
(c) a first working surface, on the first electrode surface, wherein the dielectric is present between the first working surface and the first electrode surface, and
(d) a second working surface, on the second electrode surface, wherein the dielectric is present between the second working surface and the second electrode surface,
wherein the electrode assembly has a service life of at least 300 hours at 60 kV,
the dielectric is conformal with the first electrode surface, the second electrode surface and the electrode edge, with no gas bubble defects at dielectric-electrode interfaces,
a radius of curvature of the electrode edge parallel to the first and second electrode surfaces is at least 1 inch,
a radius of curvature of the electrode edge perpendicular to the first and second electrode surfaces is at least 0.25 inches,
the first working surface comprises glass, and the second working surface comprises glass, and
the glass has a thickness of at least 1 mm.

* * * * *

UNITED STATES PATENT AND TRADEMARK OFFICE
CERTIFICATE OF CORRECTION

PATENT NO. : 10,925,144 B2
APPLICATION NO. : 16/442380
DATED : February 16, 2021
INVENTOR(S) : Mark A. Hochwalt Page 1 of 1

It is certified that error appears in the above-identified patent and that said Letters Patent is hereby corrected as shown below:

In the Claims

Column 14, Line 28, Claim 1 delete "AD" and insert --and--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*